(12) United States Patent
Renier et al.

(10) Patent No.: US 8,969,320 B2
(45) Date of Patent: Mar. 3, 2015

(54) HYALURONIC ACID DERIVATIVES CONTAINING GROUPS ABLE TO RELEASE NO

(71) Applicant: Fidia Farmaceutici S.P.A., Abano Terme (IT)

(72) Inventors: Davide Renier, Abano Terme (IT); Matteo D'Este, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 105 days.

(21) Appl. No.: 13/757,720

(22) Filed: Feb. 1, 2013

(65) Prior Publication Data
US 2013/0184235 A1 Jul. 18, 2013

Related U.S. Application Data

(62) Division of application No. 12/655,151, filed as application No. PCT/EP2008/005140 on Jun. 25, 2008, now abandoned.

(30) Foreign Application Priority Data

Jul. 5, 2007 (IT) ................ 2007A001341

(51) Int. Cl.
| | | |
|---|---|---|
| A61K 8/73 | (2006.01) | |
| A61K 31/728 | (2006.01) | |
| A61K 47/36 | (2006.01) | |
| A61K 47/48 | (2006.01) | |
| C08B 37/08 | (2006.01) | |
| A61K 9/00 | (2006.01) | |
| A61K 45/06 | (2006.01) | |

(52) U.S. Cl.
CPC ........... *A61K 47/4823* (2013.01); *A61K 31/728* (2013.01); *A61K 9/0014* (2013.01); *A61K 9/0021* (2013.01); *A61K 47/36* (2013.01); *C08B 37/0072* (2013.01); *A61K 45/06* (2013.01)
USPC .......................................... 514/54

(58) Field of Classification Search
None
See application file for complete search history.

(56) References Cited

U.S. PATENT DOCUMENTS

2005/0220756 A1   10/2005   Stamler et al.

FOREIGN PATENT DOCUMENTS

| WO | WO-98/05689 A1 | 2/1998 |
| WO | WO 98/20015 | * 5/1998 |
| WO | WO-99/67296 A1 | 12/1999 |
| WO | WO-2004/035629 A2 | 4/2004 |

OTHER PUBLICATIONS

Seabra, A. et al "Polynitrosated polyesters: preparation, characterization, and potential use for topical nitric oxide release" Biomacromolecules (2005) vol. 6, pp. 2512-2520.*
Kennedy, J.F. et al., "Chapters 8 and 9: Polysaccharides, and Glycoproteins and proteoglycans", "Bioactive Carbohydrates: In Chemistry, Biochemistry and Biology", pp. 142-229, Jan. 1, 1983.
Thierry, B. et al., "Radionuclides-hyaluronan-conjugate thromboresistant coatings . . . " Biomaterials, (2004), vol. 25, pp. 3895-3905.

* cited by examiner

*Primary Examiner* — Leigh Maier
(74) *Attorney, Agent, or Firm* — Birch, Stewart, Kolasch & Birch, LLP

(57) ABSTRACT

Disclosed are hyaluronic acid derivatives functionalized with S-nitrosothiol groups of the general formula: wherein HA indicates hyaluronic acid and G indicates a suitable spacer.

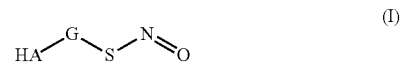

(I)

14 Claims, 3 Drawing Sheets

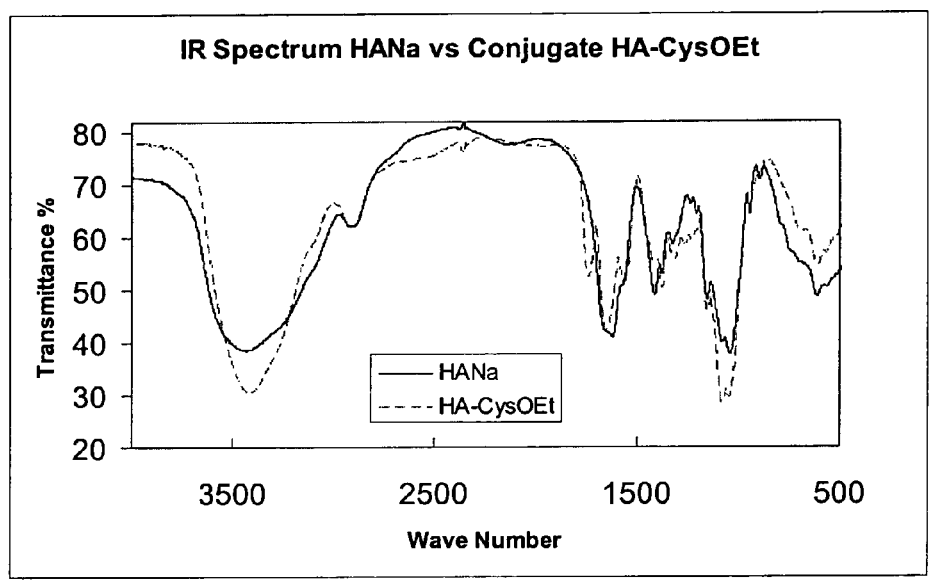
Figure 1: IR spectrum of HA-cysteine ethyl ester conjugate prepared according to the methodology summarised in scheme 6

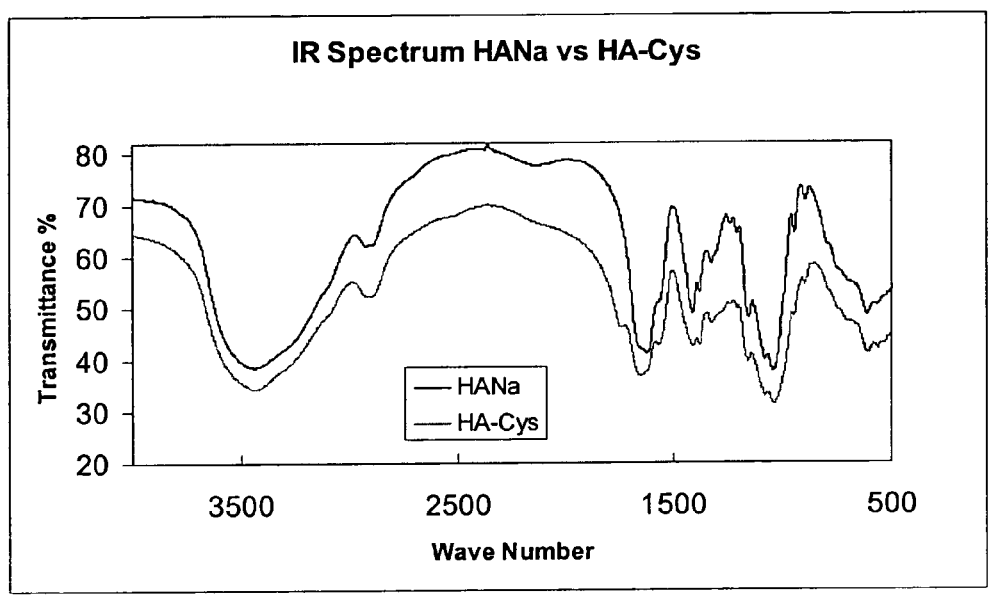
Figure 2: FTIR spectra of HA-cysteine conjugate synthesised according to scheme 6 and of HA sodium salt

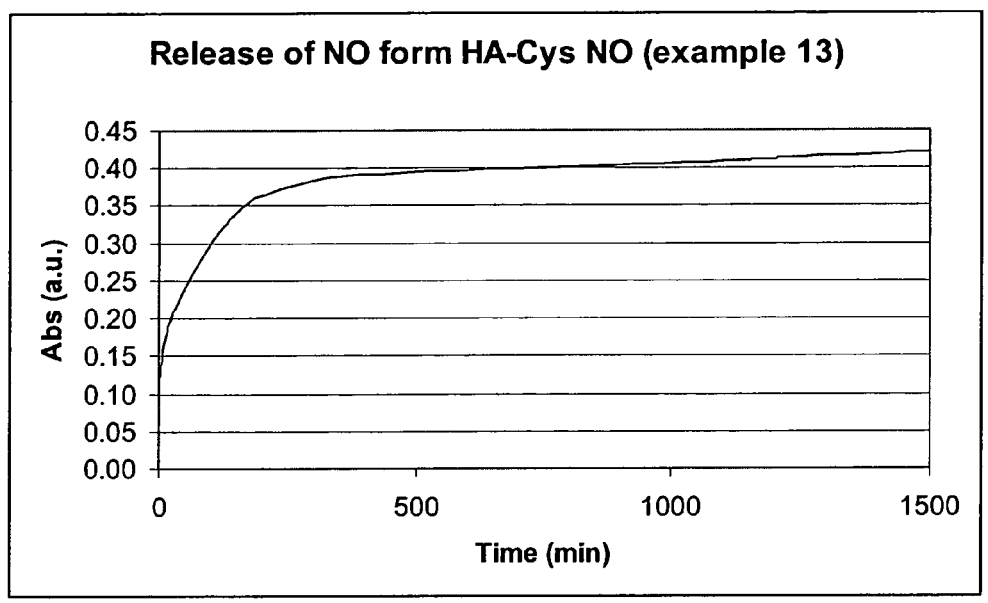
Figure 3: Time profile of NO release by the HA-cysteine conjugate referred to in example 13

HYALURONIC ACID DERIVATIVES CONTAINING GROUPS ABLE TO RELEASE NO

This application is a Divisional of co-pending application Ser. No. 12/665,151 filed on Jan. 29, 2010 and for which priority is claimed under 35 U.S.C. §120. application Ser. No. 12/665,151 is the national phase of PCT International Application No. PCT/EP2008/005140 filed on Jun. 25, 2008 under 35 U.S.C. §371, which claims priority to Italian Application No. MI2007A 1341 filed on Jul. 5, 2007. The entire contents of each of the above-identified applications are hereby incorporated by reference.

The present invention relates to derivatives of hyaluronic acid (HA) functionalised with molecules containing S-nitrosothiol groups of the general formula:

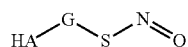

wherein HA indicates hyaluronic acid and G indicates a suitable spacer, in particular the N-acetylpenicillamine molecular fragment or cysteine (Cys).

The derivatives of the invention are able to release NO (NO-donors), and can be used advantageously in dermatological and cosmetic applications, in particular to correct skin defects and for biorevitalisation of tissues after intradermal, subcutaneous or topical administration. The derivatives according to the invention can also be used for cardiovascular applications and for the controlled release of antitumoral, antiviral or antimicrobial drugs and/or agents.

PRIOR ART

Nitrous oxide (NO) acts in numerous parts of the body, being involved in a wide range of biological activities ranging from neurotransmission to relaxation of the smooth muscles, from vasodilation to the response to immunogens, and makes a significant contribution to the maintenance of homeostasis, due to its free radical scavenging action. Of the various areas in which NO operates, the skin, where NO acts at the level of the fibroblasts, keratinocytes and the complex series of events known as wound healing, is particularly important for the purposes of this invention (Cals-Grierson, Nitric Oxide, 2004, 10, 179-193). The use of compounds which directly or indirectly release nitrogen oxides was recently proposed for a variety of applications in the pharmaceutical/medical and cosmetic fields. See, for example. WO 2006/097350, FR 2883170, WO 2006/095193, US 20040171589, EP 1442739, WO 2003/049593, EP 1001677, WO 2006/100154 and U.S. Pat. No. 6,251,594.

S-Nitroso-N-acetylpenicillamine (SNAP) of formula

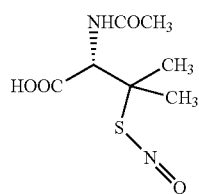

is a known commercial NO donor used mainly in biochemical and pharmacological studies (Zhang Y. et al., Free Radical Biology and Medicine 2005, volume 38, pp. 831-838 and Wang. P. G. et al., Chemical Reviews, 2002, 102, 1091-1134). For the scope of the present invention both D- (see formula) and L-enantiomer can be used indifferently.

Another molecule which is very suitable to derivatise HA, enabling the biopolymer to release nitric oxide, is cysteine. Said amino acid can be bonded to HA through an amide bond in which HA participates through the carboxyl group of glucuronic acid, and cysteine through the primary amine function. The synthesis can be performed in an aqueous medium using amide formation promoters such as water-soluble carbodiimides (e.g. 1-ethyl-3-(3-dimethylaminopropyl)-carbodiimide, EDC). The recent literature (Kafedjiiski. K et. al., Int. J. Pharmaceut. 2007, doi:10.1016/J. pharm. 2007.04.019), has demonstrated some interesting mucoadhesion properties of crosslinked derivatives prepared from HA-Cys conjugates; the authors have therefore proposed their use as multipurpose excipients for the development of drug delivery systems. The present invention, however, uses the HA-Cys conjugate in the native form, i.e. not crosslinked by subsequent derivatisation to form conjugates of the general formula:

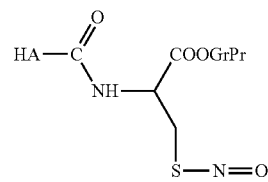

wherein GrPr indicates a generic carboxyl-protecting group, such as a methyl- or ethyl-ester.

BRIEF DESCRIPTION OF THE DRAWINGS

FIG. 1 depicts the results of the FTIR spectrum analysis of the conjugate between HA and cysteine ethyl ester and HA sodium salt.

FIG. 2 depicts the FTIR spectrum results of the conjugate between HA and cysteine and the conjugate between HA and sodium salt.

FIG. 3 depicts the time profile of NO release by the HA cysteine conjugate of Example 13.

DESCRIPTION OF THE INVENTION

It has now been found that hyaluronic acid derivatives functionalised with S-nitroso groups of formula

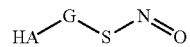

wherein HA indicates hyaluronic acid and G is a spacer between a carboxy or amino functional group of hyaluronic acid and respectively an amino or carboxy functional group of a residue comprising a thiol group, are effective donors of NO, which has a variety of uses in the pharmaceutical, cosmetic and medical fields.

Examples of G-S—N═O groups are N-acetylpenicillamine residues of formula:

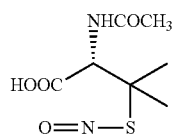

or S-nitroso cysteine residues of formula:

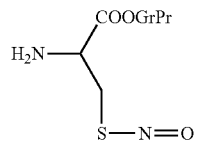

(GrPr represents a protective group such as a C1-C4-alkyl group, in particular methyl or ethyl).

The association between HA and a molecule able to release NO is advantageous for all applications which require the activation of cutaneous and/or dermal repair processes, such as lesions and superficial defects, aging and photoaging, and biorevitalisation of the dermal tissues. In these conditions, the known effects attributable to NO, such as:

- increased collagen synthesis by the keratinocytes;
- increased microcirculation;
- facilitation of keratinocyte and fibroblast proliferation;
- inducement of TGF-b1 (Transforming Growth Factor-beta 1) and IL synthesis, with consequent activation of the skin repair processes;
- stimulation of chemotactic release factors (such as VEGF—Vascular Endothelial Growth Factor);

are surprisingly optimised by the association with hyaluronic acid or a derivative thereof.

The presence of hyaluronic acid or a derivative thereof:

- allows synergic exploitation of the wound-healing, emollient, humectant, repair and filling properties of hyaluronic acid and/or its derivatives;
- in view of the modulatability of the rheological characteristics of HA as such and its derivatives, some very different pharmaceutical forms can be obtained which are totally adaptable to the site of application. Possible products are an injectable gel for intradermal and/or subcutaneous administration to treat wrinkles, scars and skin defects; hydrogels, creams, dressings or films for topical application with a wound-healing, biorevitalising and regenerating effect, gels with controlled viscosity for drug delivery, to be administered by the systemic or loco-regional (e.g. intra-articular) route, etc.
- above all, maintains the product at the site of application for longer, with consequent gradual release of NO. The conjugation between HA and/or its derivatives and the source of NO is a chemical bond, which ensures the stability of the product and guarantees that the release of NO will be constant and continuous.

Functionalisation with S-nitroso-N-acetyl-penicillamine groups may involve amine groups deriving from deacetylation of the N-acetylglucosamine residues of hyaluronic acid or amine groups introduced by esterifying the carboxyl groups of the glucuronic acid units with aminoalkyl residues.

In the first case, the derivatives according to the invention can be obtained from N-acetylpenicillamine or activated derivatives thereof, preferably from the corresponding cyclic anhydride or 3-acetamido-4,4-dimethylthioethane-2-one (cAP), obtained from N-acetyl-DL-penicillamine (AP) in the presence of pyridine and acetic anhydride according to the following reaction:

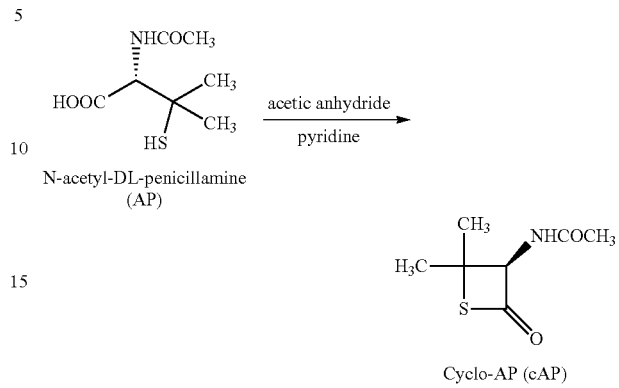

This reaction is promoted by the anhydrous medium using an excess of acetic anhydride, preferably between 4 and 5 times the moles of AP. The reaction takes place at a low temperature, between −20° and 5° C., preferably 0° C., in a time interval of between 10 and 120 min, preferably 30 min. The compound cAP (3-acetamide-4,4-dimethylthioethane-2-one) is separated from the reaction mixture by adding a chlorinated organic solvent, preferably dichloromethane or chloroform.

The cAP thus obtained can therefore be reacted with partly deacetylated hyaluronic acid or with aminoalkylesters of hyaluronic acid obtainable from alkaline salts, preferably sodium salts, of hyaluronic acid which, after transformation to a tetraalkylammonium salt, preferably tetrabutyl ammonium (TBA), through ion exchange and possibly subsequent freeze-drying, are reacted with compounds of formula X-A-$NH_2$ wherein X is a halogen atom, preferably bromine, and A is an aliphatic or arylaliphatic spacer residue having 2 to 16 carbon atoms, preferably a —$(CH_2)_n$— group, wherein n is an integer between 2 and 16, and preferably between 2 and 7.

Specific examples of compounds of formula X—$(CH_2)_n$—$NH_2$ are 2-bromo-1-ethylamine, 3-bromo-1-propylamine, and 7-bromo-1-heptylamine. These diamines are used in the form of salts, such as halohydrates.

Finally, the derivatives of the invention are obtained by subsequent treatment with an alkyl nitrite.

The processes described above are illustrated in the following Schemes;

Scheme 1: Preparation of HA aminoalkyl ester

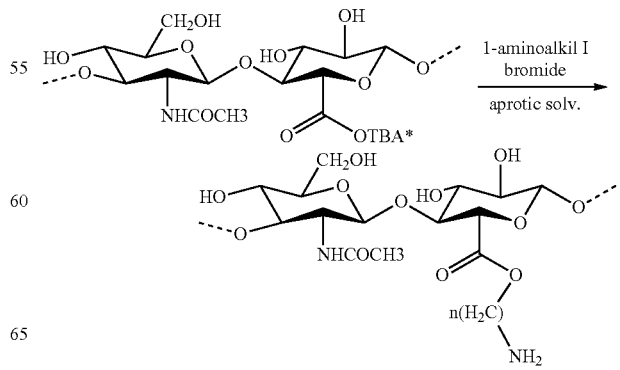

Scheme 2: Preparation of the derivatives of the invention from HA aminoalkylesters
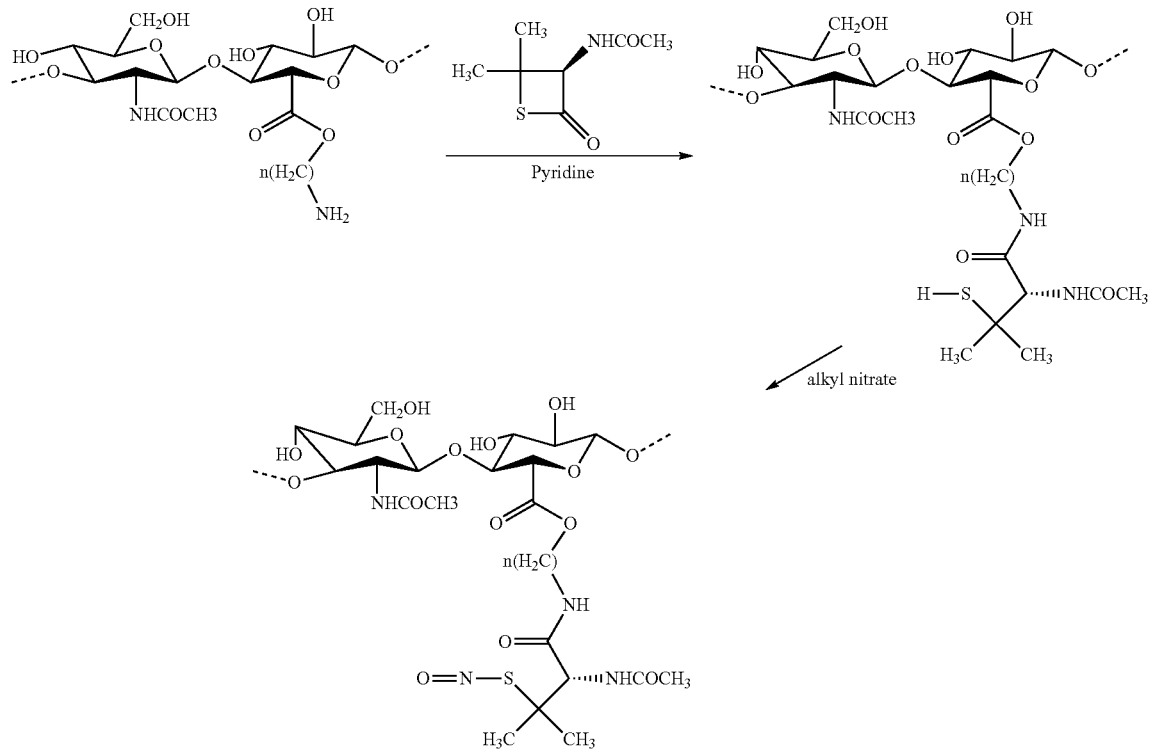
Scheme 3: Deacetylation of HA
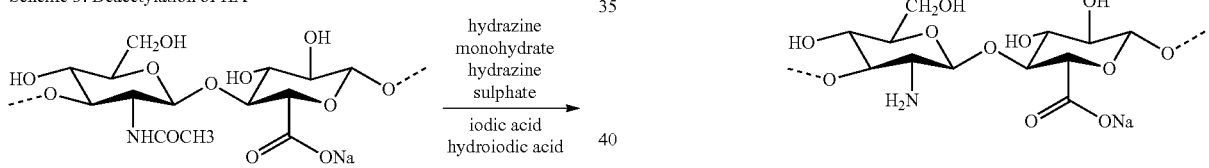
Scheme 4: Preparation of the derivatives of the invention from partly deacetylated HA
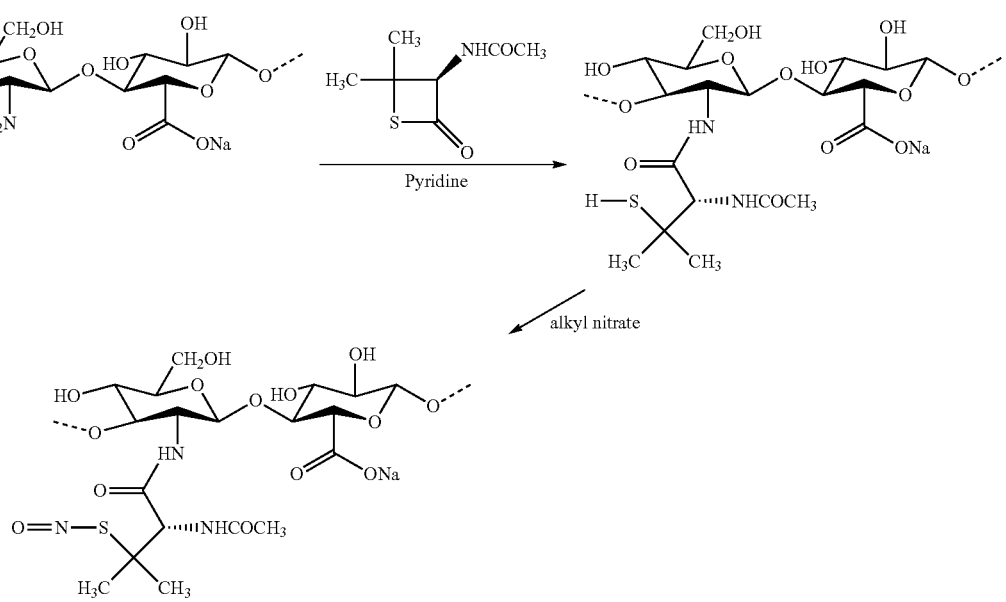
-continued
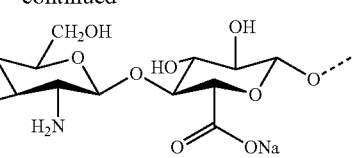

More particularly, to prepare aminoalkylesters, the HA-TBA salt is solubilised in an aprotic solvent such as N-methyl-pyrrolidone (NMP), N,N-dimethylformamide (DMF) or DMSO, in concentrations ranging between 3 and 25 mg/ml, depending on the molecular weight of the HA. Halo-alkylamine is added to the reaction mixture in an almost stoichiometric amount, in agreement with the substitution degree required.

The reaction proceeds at a temperature of 25 to 40° C. for a time from 24 to 96 hrs. Finally, the ester is separated from the reaction mixture by alcoholic precipitation, preferably with ethanol, after ion exchange between the tetraalkylammonium salt and sodium.

After drying, the product is dissolved in DMF together with cAP in a 1:1 stoichiometric ratio to the —$NH_2$ groups of the ester conjugate of HA, and the reaction proceeds for at least 30 min, after which the solvent is removed. The product is taken up again in DMF, and an excess of alkyl nitrite, preferably isopentyl nitrite, is added. The reaction proceeds at a low temperature, preferably −20° C.

The product is recovered by alcohol precipitation, preferably with 95° ethanol, and washed with absolute ethanol. The ester conjugate HA-SNAP is obtained in this way.

For the preparation of derivatives from partly de-N-acetylated HA, HA is solubilised in hydrazine or hydrazine hydrate with a purity of not less than 95%, at a concentration of between 1 and 50 mg/ml, and preferably between 5 and 25 mg/ml. An amount of hydrazine sulphate between 0.1 and 3% w/v, preferably 1%, is added to the resulting solution.

The reaction is carried out at a temperature interval between 40 and 90° C., preferably 60° C., under constant stirring. The reaction time depends on the percentage of de-N-acetylation to be obtained, but is between a few hrs and 50 hrs. The reaction is then arrested by precipitation with a polar solvent, preferably ethanol. The precipitate is partly dried under vacuum, and treated with iodic acid having a molar concentration of between 0.1 and 1 M, preferably 0.5 M, and then with 57% (w/v) hydroiodic acid. The pH of the solution is maintained between 5 and 7 by adding a 10% (w/v) solution of sodium acetate.

The aqueous phase containing the modified polysaccharide is subjected to repeated extraction with ethyl ether, until complete decolouring of the aqueous phase (initially dark yellow-brown). Finally, it is precipitated with a polar solvent, preferably ethanol. The product, recovered as a white precipitate, is dried under vacuum for at least 48-72 hrs at 30° C.

Derivatisation of HA with S-nitroso cysteine residues comprises 2 synthesis steps: reaction between HA and cysteine (Cys) and subsequent transformation to the S-nitroso derivative.

The reaction between the biopolymer and the amino acid is conveniently carried out starting from cysteine or derivatives, such as its carboxyl esters (wherein Cys participates in the ester bond as acid) or thioesters (wherein Cys participates in the thioester bond as thiol). Cys or its derivatives are reacted with hyaluronic acid or its alkaline salts, preferably the sodium salt, in an aqueous medium. Alternatively, the reaction can be conducted in an aprotic polar solvent such as N-methyl-pyrrolidone (NMP), N,N-dimethylformamide (DMF) or dimethyl sulphoxide (DMSO) using an HA tetraalkylammonium salt. These salts are obtainable from alkaline salts, preferably sodium salts, of HA through ion exchange and possibly freeze-drying.

The formation of the amide bond between HA and Cys is promoted by adding to the reaction mixture an activating agent such as a carbodiimide, or carbonyldiimidazole, or more generally using any activating agent classically employed in peptide synthesis. If the reaction is conducted in water. Cys and HA or its alkaline salts are reacted through 1-ethyl-3-(3-dimethylaminopropyl)-carbodiimide (EDC) in the presence of N-hydroxysuccinimide (NHS). In the absence of NHS the reaction would begin through the formation of O-acylisourea, an unstable intermediate with a tendency to rearrange to give N-acylurea, a compound which is no longer reactive towards amines. The addition of NHS allows the formation of an intermediate in the form of a non-rearrangeable activated ester, making coupling the primary amine to HA possible (J Biomed Mater Res. 1999 November; 47(2): 152-169 PMID:10449626). The reaction proceeds at a pH of less than 8, and is promoted by a slightly acid pH. The preparation is carried out at a temperature between 0 and 45° C. and completed in less than 24 hrs, after which the conjugate is isolated by precipitation with a solvent consisting of a water-alcohol mixture, alcohol-acetone or alcohol. The derivative can be purified by repeated washing with a water-alcohol mixture directly on the solid, or by dialysis.

The processes described above are illustrated in the following schemes:

Scheme 5: Preparation of HA-cysteine conjugate in water

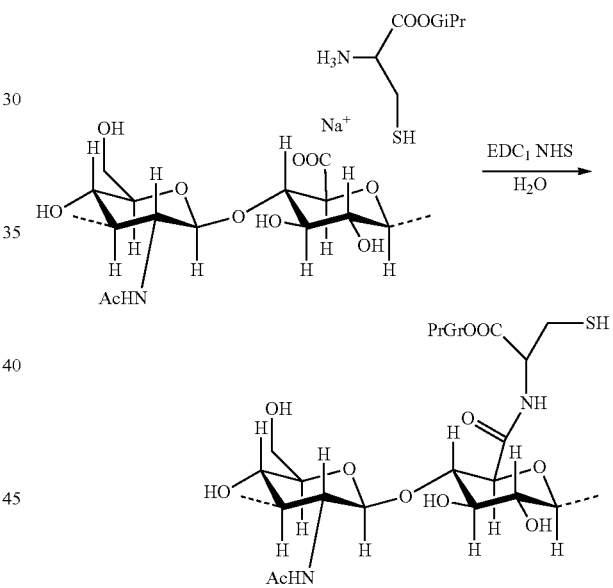

Scheme 6: Preparation of HA-cysteine conjugate in aprotic polar solvent

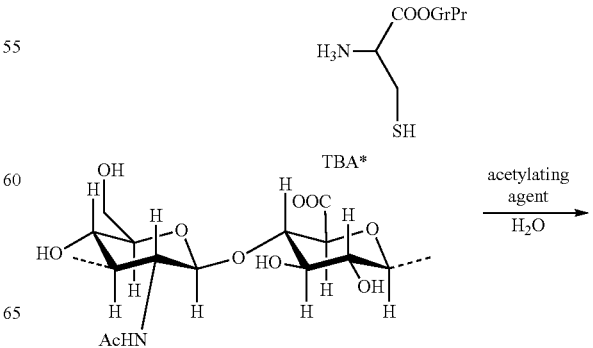

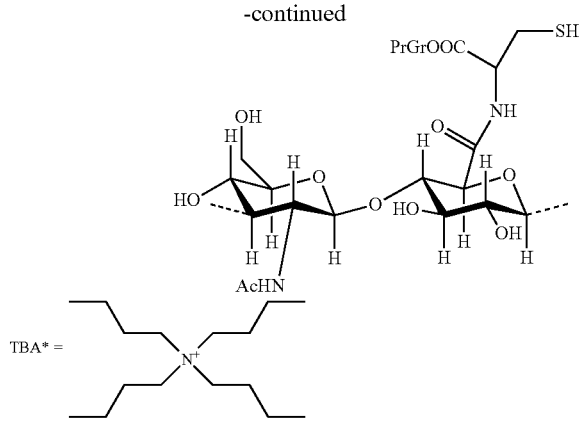

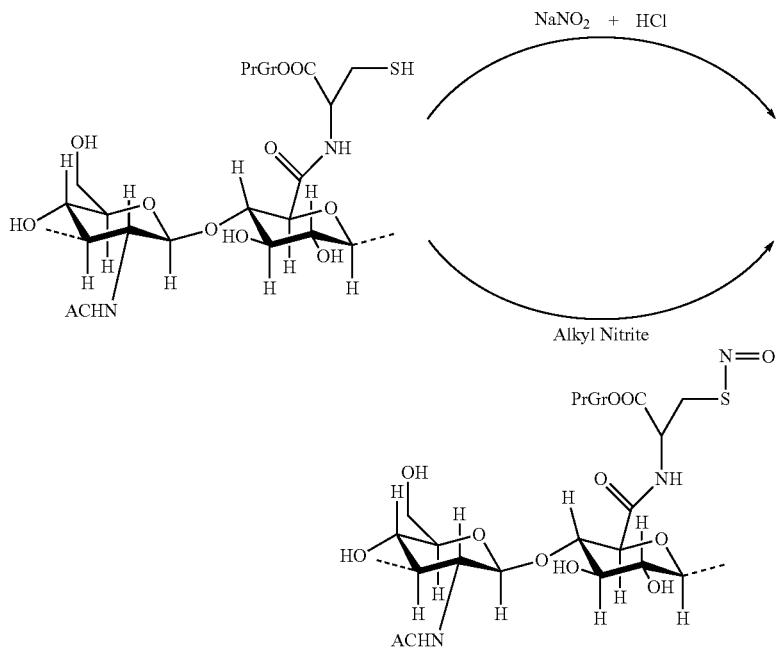

Scheme 7: Preparation of the derivatives of the invention from HA-cysteine conjugate In particular, the HA-Cys conjugate (Scheme 5) is synthesised by solubilising HA (or its alkaline salts) in water to a concentration of between 1 and 50 mg/ml, preferably between 3 and 25 mg/ml; an amount of HCl/NaOH at the concentration of between 0.1 and 1M is added to the solution thus obtained to adjust the pH to the interval 5.0-6.0, and preferably around 5.5. At this point EDC. NHS, and Cys preferably in the form of ethyl ester are added. The protected amino acid is added in a stoichiometric amount in relation to the substitution degree to be obtained, whereas EDC and NHS are added in slight stoichiometric excess compared with the cysteine. Before the reaction mixture is incubated, the pH is further corrected to a value between 5 and 7, and preferably around 6. Synthesis is carried out at a temperature of between 0 and 45° C., for between 4 and 24 hrs, after which an amount of precipitant corresponding to between 3 and 10 times the volume of the reaction mixture is added to said mixture. The precipitating solvent consists of mixtures of polar solvents such as alcohols or acetone. The product is isolated by filtration or decanting, then washed until elimination of the ion content in solution, as verified by the specific conductivity of the washing water, which should reach a value of less than 30 µS/cm. The last wash is performed with absolute ethanol.

Alternatively, purification can be performed by dialysis against a NaCl solution with a concentration of between 0.5 and 5% w/v, preferably 1%, or against demineralised water. The product is then isolated as a solid by freeze-drying.

If the reaction is conducted in aprotic polar solvent (scheme 6) instead of water, carbodiimides such as N,N'-dicyclohexylcarbodiimide, N,N'-di-isopropylcarbodiimide, N,N'-di-toluylcarbodiimide, or carbonyldiimidazole in the presence of methanesulfonic acid can be used to promote acylation of the primary amine group of the cysteine.

In this case the starting hyaluronic acid in the form of a tetraalkyl ammonium salt, preferably tetrabutyl ammonium, is dissolved in the aprotic solvent (NMP, DMF or DMSO) in concentrations ranging between 1 and 25 mg/ml, depending on the molecular weight of the HA. Cys, preferably in the form of ethyl ester, is added to the reaction mixture in a stoichiometric amount or in slight excess compared with the substitution degree desired, together with the corresponding activating agent. The reaction proceeds at a temperature of between 0 and 45° C., for less than 24 hrs. At this stage the product is in the form of a partial ester of hyaluronic acid, the remaining carboxyl groups being accompanied by tetrabutylammonium counter-ions. An exchange is made with sodium ions by adding a volume of a saturated solution of sodium chloride or sodium bromide amounting to 5-10% of the volume of the reaction mixture, and leaving it under stirring for not less than 30 minutes. The product is precipitated by adding 3 to 10 volumes of mixtures of polar solvents such as alcohols or acetone, after which it is isolated by filtration or decanting, and then washed until the ion content in solution has been eliminated, as verified by the specific conductivity of the washing water, which must not exceed 30 µS/cm. The last wash is performed with absolute ethanol.

The HA-Cys derivative should be protected against air and humidity, preferably by storing it in a refrigerator at a temperature of between 2 and 8° C.

The HA-Cys conjugate is then transformed into the S-nitroso derivative (Scheme 7). Said transformation can be effected by reaction with $HNO_2$, generated in situ by acidification of $NaNO_2$ with HCl or by reaction with an alkyl nitrite.

The synthesis is conducted at a temperature of between −5° C. and 25° C. in aqueous solvent, or in water/ether solvent mixtures such as tetrahydrofuran (THF) or dioxane, and is completed in 24-48 hrs.

The product is isolated by precipitation by adding ethanol/water mixtures (preferably ethanol/water 96/4) or methanol-acetone, preferably in the ratio of 2/1 or 1/1.

The HA used in this invention may derive from any source; for example, it may be produced by extraction from rooster combs (EP 138572 B1), fermentation (EP 716688 B1) or biotechnology, and have a molecular weight of between 400 and $3 \times 10^6$ Da, preferably between $1 \times 10^5$ Da and $1 \times 10^6$ Da, and even more preferably between 200,000 and 750,000 Da.

The derivatisation reaction according to the invention can be applied both to the polysaccharide as is, and to the polysaccharide previously modified. Molecular networks will therefore be obtained from hyaluronic acid which are variously modified in accordance with known methods, in particular:

HA salified with organic and/or inorganic bases (EP 138572 B1);

HYAFF®: HA esters with alcohols of the aliphatic, arylaliphatic, cycloaliphatic, aromatic, cyclic and heterocyclic series, with an esterification percentage which can vary, depending on the type and length of the alcohol used, preferably between 50 and 100%, while the remaining percentage of non-esterified HA can be salified with organic and/or inorganic bases (EP 216453 B1);

HYADD®: HA amides with amines of the aliphatic, arylaliphatic, cycloaliphatic, aromatic, cyclic and heterocyclic series, with an amidation percentage ranging between 0.1 and 50%, while the remaining percentage of non-amidated HA can be salified with organic and/or inorganic bases (EP 1095064 B1);

O-sulphated derivatives of HA up to the 4th degree of sulphation (EP 702699 B1);

ACP®: internal esters of HA with an esterification percentage not exceeding 20%, preferably between 0.05 and 10% of esterification, while the remaining percentage of non-esterified HA can be salified with organic and/or inorganic bases (EP 341745 B1);

HA deacetylates: derive from deacetylation of the N-acetyl-glucosamine residues present in HA, with a deacetylation percentage preferably between 0.1 and 30%, while all the carboxyl groups of HA can be salified with organic and/or inorganic bases (EP 1313772 B1);

HYOXX™: percarboxylated derivatives of HA obtained by oxidation of the primary hydroxyl of the N-acetyl-glucosamine fraction with a degree of percarboxylation of between 0.1 and 100%, and preferably between 25 and 75%. All the carboxyl groups of HA can be salified with organic and/or inorganic bases (EP 1339753 A).

As already stated, the derivatives according to the invention, obtained after derivatisation of hyaluronic acid, retain the biological properties of the starting polysaccharide, but have different mechanical and rheological properties. It is therefore possible to select the most suitable derivative, depending on the type of application chosen for the end product.

The invention is described in greater detail in the examples below.

EXAMPLE 1

Preparation of HA-propylamine Ester Derivative (200 kDa)

5.00 g of extractive hyaluronic acid sodium salt hyalastine fraction (Mw approx. 200 kDa) is dissolved in 250 ml of water, and the resulting solution is percolated through a glass column pre-packed with 100 $cm^3$ of Dowex resin in the form of tetrabutylammonium. The eluted solution of HA TBA salt is collected and freeze-dried. 7.50 g of product is obtained, and dissolved in 400 ml of N-methyl-pyrrolidone (NMP).

After complete solubilisation of the HA salt, 0.53 g of 3-bromo-1-propanamine hydrobromide are added and the mixture is left to react at 35° C. for 48 h under gentle stirring. Finally, the reaction is arrested by adding 0.1 volumes of a NaCl saturated aqueous solution; 30 min later, 3 volumes of absolute ethanol are added to the solution to separate the HA ester from the reaction mixture. The precipitate is washed again with ethanol, and finally dried under high vacuum at 40° C. 4.49 g of HA-COO$(CH_2)_3$.$NH_2$ ester derivative is obtained. The substitution degree is 25% moles/moles.

EXAMPLE 2

Preparation of HA-ethylamine Ester Derivative (750 kDa)

3.00 g of extractive hyaluronic acid sodium salt, hyalectin fraction (Mw approx. 750 kDa), is dissolved in 600 ml of water, and the resulting solution is percolated through a glass column pre-packed with 100 $cm^3$ of Dowex resin in the form of tetrabutylammonium. The eluted solution of HA TBA salt is collected and freeze-dried. 4.20 g of product is obtained, and dissolved in 400 ml of N-methyl-pyrrolidone (NMP).

After complete solubilisation of the HA salt, 0.90 g of 2-bromoethylamine hydrobromide are added, and leave the mixture to react at 35° C. for 48 h under gentle stirring. Finally, the reaction is arrested by adding 0.1 volumes of a NaCl saturated aqueous solution; 30 min later, 2.5 volumes of absolute ethanol are added to the solution to separate the HA ester from the reaction mixture. The precipitate is washed again in ethanol, and finally dried under high vacuum at 40° C. 2.25 g of HA-COO$(CH_2)_2$.$NH_2$ ester derivative is obtained. The substitution degree is 50% moles/moles.

EXAMPLE 3

Preparation of HA-heptylamine Ester Derivative (15 kDa)

6.00 g of fermentative hyaluronic acid sodium salt, LMW (Low Molecular Weight) fraction (15 kDa), is dissolved in 300 ml of water, and the resulting solution is percolated through a glass column pre-packed with 120 $cm^3$ of Dowex resin in the form of tetrabutylammonium. The eluted solution of HA TBA salt is collected and freeze-dried. 8.43 g of the product is obtained, and dissolved in 420 ml of N,N dimethylformamide (DMF).

After complete solubilisation of the LMW HA salt, 0.66 g of 7-bromoheptylamine hydrobromide are added and left to react at 35° C. for 72 h under gentle stirring. Finally, the reaction is arrested by adding 0.1 volumes of a NaCl saturated aqueous solution; 30 min later, 2.5 volumes of absolute ethanol are added to the solution to separate the HA ester from the reaction mixture. The precipitate is washed again in ethanol, and finally dried under high vacuum at 40° C. 4.70 g of HA-COO(CH$_2$)$_7$.NH$_2$ ester derivative is obtained. The substitution degree is 10% moles/moles.

EXAMPLE 4

Preparation of HA-propyl-SNAPp25 Ester Derivative 4.00 g of N-acetyl-DL-penicillamine compound (AP) is dissolved in 8 ml of pyridine in the presence of 8 ml of acetic anhydride. The reaction proceeds for 30 min at 0° C. and overnight at room temperature, always under gentle stirring. The reaction is arrested by evaporation, and the residue is taken up with at least 100 ml of dichloromethane. Then the organic solution is extracted at least 3 times with 50 ml of an aqueous acid solution (approx. 1 M HCl), filtered, and finally evaporated to dryness. The residue is washed with 50 ml of ethyl ether. 1.80 g of cyclic cAP derivative (3-acetamide-4, 4-dimethylthioethane-2-one) is obtained.

4.00 g of the derivative obtained as described in Example 1 and 1.70 g of cAP are dissolved in 200 ml of DMF, and stirring is maintained for 30 min at room temperature. After removal of the solvent, the residue is taken up with the minimum volume of DMF and treated with isopentyl nitrite at −20° C. for 2 hrs. Temperature is increased to between 15 and 25° C., the mixture is precipitated in 3 volumes of ethanol, and the product is washed with absolute ethanol. After drying under high vacuum, 4.11 g of HA-propyl-SNAPp25 ester derivative is obtained.

EXAMPLE 5

Preparation of HA-ethyl-SNAPp50 Ester Derivative 3.00 g of N-acetyl-DL-penicillamine compound (AP) is dissolved in 6 ml of pyridine in the presence of 6 ml of acetic anhydride. The reaction proceeds for 30 min at 0° C. and overnight at room temperature, always under gentle stirring. The reaction is arrested by evaporation, and the residue is taken up with at least 80 ml of dichloromethane. Then the organic solution is extracted at least 3 times with 50 ml of an aqueous acid solution (approx. 1 M HCl), filtered, and finally evaporated to dryness. The residue is washed with 50 ml of ethyl ether. 1.21 g of cyclic cAP derivative (3-acetamide-4, 4-dimethylthioethane-2-one) is obtained.

2.00 g of the derivative obtained as described in Example 2 and 1.10 g of cAP are dissolved in 100 ml of DMF, and stirring is maintained for 30 min at room temperature. After removal of the solvent, the residue is taken up with the minimum volume of DMF and treated with isopentyl nitrite at −20° C. for 2 h. Temperature is increased to between 15 and 25° C., the mixture is precipitated in 3 volumes of ethanol, and the product is washed with absolute ethanol. After drying under high vacuum. 2.27 g of HA-ethyl-SNAPp50 ester derivative is obtained.

EXAMPLE 6

Preparation of HA-heptyl-SNAPp10 Ester Derivative 2.00 g of N-acetyl-DL-penicillamine compound (AP) is dissolved in 4 ml of pyridine in the presence of 4 ml of acetic anhydride. The reaction proceeds for 30 min at 0° C. and overnight at room temperature, always under gentle stirring. The reaction is arrested by evaporation, and the residue is taken up with at least 60 ml of dichloromethane. Then the organic solution is extracted at least 3 times with 50 ml of an aqueous acid solution (approx. 1 M HCl), filtered, and finally evaporated to dryness. The residue is washed with 50 ml of ethyl ether. 0.90 g of cyclic cAP derivative (3-acetamide-4, 4-dimethylthioethane-2-one) is obtained.

4.00 g of the derivative obtained as described in Example 3 and 0.70 g of cAP are dissolved in 200 ml of DMF, and stirring is maintained for 30 min at room temperature. After removal of the solvent, the residue is taken up with the minimum volume of DMF and treated with isopentyl nitrite at −20° C. for 2 h. Temperature is increased to between 15 and 25° C., the mixture is precipitated in 3 volumes of ethanol, and the product is washed with absolute ethanol. After drying under high vacuum. 3.25 g of HA-heptyl-SNAPp10 ester derivative is obtained.

EXAMPLE 7

Preparation of 23% HA-De-N Acetylate Derivative 1.00 g of fermentative HA with a molecular weight of 210 kDa is dissolved in 100 ml of hydrazine monohydrate together with 1.00 g of hydrazine sulphate. The solution is maintained under stirring for 48 h at 60° C., then the reaction is arrested by adding 150 ml of ethanol. The precipitate in gel form is washed and dried dry at room temperature overnight.

Then the intermediate is redissolved in 100 ml of distilled water and 20 ml of 10% w/v sodium acetate solution, and 30 ml of a 0.5 M iodic acid solution is added. After 30 minutes, 5 ml of 57% hydriodic acid is added. During this last operation, the temperature is maintained at 0° C. with an ice bath.

The aqueous solution, which has a deep brown colour, is treated by liquid-liquid extraction at least five times with 50 ml of ethyl ether. Finally, the pH of the decoloured solution containing the modified polysaccharide is adjusted to between 6.5 and 7 with 1 N NaOH, and the product is precipitated with 200 ml of ethanol. The white precipitate is washed with ethanol and dried under vacuum for at least 48 hrs. 0.94 g of HA-De-acetylate is obtained, and the degree of deacetylation is 23%.

EXAMPLE 8

Preparation of HA-N-SNAPp23 Derivative 2.00 g of N-acetyl-DL-penicillamine compound (AP) is dissolved in 4 ml of pyridine in the presence of 4 ml of acetic anhydride. The reaction proceeds for 30 min at 0° C. and overnight at room temperature, always under gentle stirring. The reaction is arrested by evaporation, and the residue is taken up with at least 60 ml of dichloromethane. Then the organic solution is extracted at least 3 times with 50 ml of an aqueous acid solution (approx. 1 M HCl), filtered, and finally evaporated to dryness. The residue is washed with 50 ml of ethyl ether. 0.92 g of cyclic cAP derivative (3-acetamide-4, 4-dimethylethane-2-one) is obtained.

0.80 g of the derivative obtained as described in Example 7 and 0.70 g of cAP are dissolved in 100 ml of DMF, and stirring is maintained for 30 min at room temperature. After removal of the solvent, the residue is taken up with the minimum volume of DMF and treated with isopentyl nitrite at −20° C. for 2 h. Temperature is increased to between 15 and 25° C., the mixture is precipitated in 3 volumes of ethanol, and washed with absolute ethanol. After drying under high vacuum. 1.04 g of HA-N-SNAPp23 derivative is obtained.

EXAMPLE 9

Preparation of HA-Cys p25 Derivative (200 kDa)

5.00 g of fermentative hyaluronic acid sodium salt, hyalastine fraction (Mw 200 kDa), is dissolved in 300 ml of water. The solution is added with an amount of 1M HCl/NaOH sufficient to adjust the pH to 5.5. 0.60 g of cysteine-ethyl ester hydrochloride, 0.61 g of EDC and 0.36 g of NHS are added; when they have dissolved, the pH of the reaction mixture is adjusted to around 6. The mixture is left to react at room temperature (24° C.) for 24 hrs, periodically checking the pH, and adjusting if necessary with 0.1 M HCl/NaOH to maintain the value at around 6. At the end of the reaction, the pH is adjusted to around 7, and the product is precipitated with 4 volumes of 96% ethanol.

The product is recovered by filtration and washed with 8/2, then 9/1 mixtures of ethanol/water until elimination of the content of ions in solution, as verified by the specific conductivity of the washing water, which should reach a value of less than 30 µS/cm. After a last wash with absolute ethanol, the product is dried under vacuum at 40° C. to constant weight. The product appears as a white hygroscopic solid, weighing 4.44 g. It should be stored under nitrogen atmosphere at a Temperature below 6° C. The substitution degree is 24% moles/moles.

EXAMPLE 10

Preparation of HA-Cys p50 Derivative (750 kDa)

3.00 g of extractive hyaluronic acid sodium salt, hyalectin fraction (Mw approx. 750 kDa), is dissolved in 600 ml of water, and the resulting solution is percolated through a glass column pre-packed with 100 cm$^3$ of Dowex resin in the form of tetrabutylammonium. The eluted solution of HA TBA salt is collected and freeze-dried. 4.12 g of product is obtained, and dissolved in 450 ml of DMSO. 0.60 g of cysteine-ethyl ester hydrochloride and 0.70 g of N,N'-di-cyclohexylcarbodiimide (DCC) are added. The mixture is left to react at room temperature (24° C.) for 24 hrs, and slowly added with 50 ml of saturated NaCl solution (330 g/l). The product is precipitated by slowly adding 2 l of 96° ethanol. The product is washed with an 8/2 ethanol/water mixture to a specific conductivity of less than 30 µS/cm, then washed with absolute ethanol and dried under vacuum at 40° C. to constant weight. The product appears as a white hygroscopic solid, weighing 3.09 g. It should be stored under nitrogen atmosphere at a Temperature below 6° C. The substitution degree is 47% by moles.

EXAMPLE 11

Preparation of LMW HA-Cys p50 Derivative 5.00 g of fermentative hyaluronic acid sodium salt with a low molecular weight (Mw 15 kDa) is dissolved in 250 ml of water. The solution is added with an amount of 1M HCl/NaOH sufficient to adjust the pH to 5.5. Add 1.20 g of cysteine-ethyl ester hydrochloride, 1.22 g of EDC and 0.72 g of NHS; when they have dissolved, the pH of the reaction mixture is adjusted to around 6. The mixture is left to react at room temperature (24° C.) for 24 hrs, taking care to check the pH periodically, and correct if necessary with 0.1 M HCl/NaOH to maintain the value at around 6. At the end of the reaction, the pH is adjusted to around 7, and the product is precipitated with 3 volumes of 1/1 methanol/acetone mixture.

The product is recovered by filtration, then washed with 96% ethanol until elimination of the content of ions in solution, as verified by the specific conductivity of the washing water, which should reach a value of less than 30 µS/cm. After a last wash with absolute ethanol, the product is dried under vacuum at 40° C. to constant weight. The product appears as a white hygroscopic solid, weighing 4.32 g. It should be stored under nitrogen atmosphere at a Temperature below 6° C. The substitution degree is 52% moles/moles.

EXAMPLE 12

Preparation of LMW HA-Cys-S-nitric Oxide p50 Derivative 4.00 g of the product obtained as described in example 11 are dissolved in 250 ml of water. 0.50 g of sodium nitrite $NaNO_2$ is added, the reaction mixture is cooled to the temperature of 5° C. and slowly added with 7.2 ml of 1N HCl. After 2 hrs, the mixture is left to heat (warm) to room temperature. The product is recovered by precipitation with 96% ethanol, washed with the same solvent, and dried at 40° C. under vacuum. 3.87 g of the product is obtained, which should be stored under nitrogen atmosphere at a Temperature below 6° C.

EXAMPLE 13

Preparation of HA-Cys-S-nitric Oxide p50 Derivative (750 kDa)

3.00 g of the product obtained as described in example 10 is dissolved in 350 ml of water. 0.30 g of sodium nitrite $NaNO_2$ is added, the reaction mixture is cooled to the temperature of 5° C. and slowly added with 4.3 ml of 1N HCl. After 2 hrs, the mixture is left to warm to room temperature. The product is recovered by precipitation with 96% ethanol, washed with the same solvent, and dried at 40° C. under vacuum. 2.69 g of the product is obtained, which should be stored under nitrogen atmosphere at a Temperature below 6° C.

EXAMPLE 14

Preparation of LMW HA-Cys-S-nitric Oxide p50 Derivative via Alkyl Nitrite 4.00 g of the product obtained as described in example 11 is dissolved in the minimum amount of DMF. The mixture is treated with isopentyl nitrite at −20° C. for 2 h. The product is recovered by precipitation with 3 volumes of 96% ethanol, washed with the same solvent, and dried at 40° C. under vacuum. 3.61 g of the product is obtained, which should be stored under nitrogen atmosphere at a Temperature below 6° C.

EXAMPLE 15

Characterisation of the Compounds by FTIR

FIG. 1 shows the FTIR spectrum (Jasco FT/IR-4100 spectrophotometer) of the conjugate between HA and cysteine ethyl ester (broken line) and HA sodium salt (continuous line). In the region of the wave numbers around 1700 cm$^{-1}$ (carbonyl bond stretching modes) a new band is evident at 1740 cm$^{-1}$, which was not observed in the starting reagents.

This indicates the formation of a covalent bond between the biopolymer and the protected amino acid.

FIG. 2 compares the FTIR spectrum of the conjugate between HA and cysteine and HA sodium salt. Once again, the most significant difference is the presence of a new band not found in the starting reagents, located at 1735 cm$^{-1}$, and attributable to the formation of the new covalent species.

EXAMPLE 16

Release Test

The nitric oxide (NO) release profile of the compounds of the invention was evaluated by spectrophotometry using the Guess test. The trend of NO release by the HA-Cys conjugate in S-nitroso form, prepared as described in example 13, is shown here by way of example. Briefly: 4 mg of the product is dissolved in 2.5 ml of Griess reagent in a UV-visible spectrophotometric cuvette. The solution is rapidly homogenised, placed in a double-beam spectrophotometer (Perkin Elmer Lambda 2), and the absorbance trend is measured at 540 nm over time against a blank consisting of Griess solution. The results are shown in FIG. 3. The absorbance, i.e. the nitric oxide concentration, increases in the solution with an asymptotic trend, the plateau of which has not yet been reached 25 hrs after release. Assuming first-order kinetics, a decay constant amounting to 70 min$^{-1}$ is obtained.

The gradual release of NO combined with the wound-healing, emollient, humectant, repair and filling properties of hyaluronic acid and/or derivatives thereof make the compounds of the invention particularly suitable for use in dermatological, cosmetic and cardiovascular applications and for the controlled release of drugs.

The invention claimed is:

1. A method for the treatment of skin lesions or defects, biorevitalisation of tissue or tissue healing which method comprises administering to a patient in need at least one hyaluronic acid compound functionalized with S-nitrosothiol groups of the general formula:

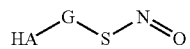

wherein HA indicates hyaluronic acid or a derivative thereof and G indicates a suitable spacer.

2. The method according to claim 1, wherein G-S—N═O represents an S-nitrosothiol acetylpenicillamine residue of formula:

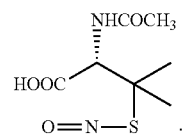

3. The method according to claim 1, wherein G-S—N═O represents S-nitro cysteine or an S-nitroso cysteine residue of formula:

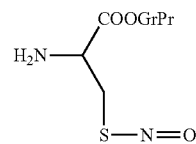

wherein GrPr represents a protective group.

4. The method according to claim 2, wherein the functionalisation of hyaluronic acid or a derivative thereof comprises amine groups prepared by deacetylation of the N-acetylglucosamine residues of hyaluronic acid or a derivative thereof, or amine groups introduced by esterifying the carboxyl groups of the glucuronic acid units of hyaluronic acid or a derivative thereof with aminoalkyl residues.

5. The method according to claim 3, wherein the functionalisation of hyaluronic acid or a derivative thereof comprises deacetylation of the N-acetylglucosamine residues of hyaluronic acid or a derivative thereof or the functionalisation of the carboxyl groups present in the glucuronic acid residues of hyaluronic acid or a derivative thereof.

6. The method according to claim 1, wherein the hyaluronic acid has a molecular weight of between 400 and $3 \times 10^6$ Da.

7. The method according to claim 4, wherein the functionalisation of hyaluronic acid or a derivative thereof comprises amine groups introduced by esterifying the carboxyl groups of the glucuronic acid units with residues of formula X-A-NH$_2$, wherein X is a halogen atom and A is an aliphatic, or arylaliphatic spacer residue having 2 to 16 carbon atoms.

8. The method according to claim 1, wherein said hyaluronic acid derivative is a member selected from the group consisting of (a) a hyaluronic acid salified with an organic and/or inorganic base, (b) a hyaluronic acid ester with an aliphatic, aryliphatic, cycloaliphatic, aromatic, cyclic or heterocyclic alcohol, (e) a hyaluronic acid amide with an aliphatic, cycloaliphatic, aromatic, cyclic or heterocyclic amine, (d) an O-sulphated hyaluronic acid derivative, (e) an internal ester of hyaluronic acid with an esterification percentage of not greater than 20%, (f) a deacetylated hyaluronic acid derivative, and (g) a percarboxylated hyaluronic acid derivative.

9. The method according to claim 6, wherein the hyaluronic acid has a molecular weight of between $1 \times 10^5$ Da and $1 \times 10^6$ Da.

10. The method according to claim 6, wherein the hyaluronic acid has a molecular weight of between 200,000 and 750,000 Da.

11. The method according to claim 7, wherein X is bromine and A is a —(CH$_2$)$_n$— group where n is an integer between 2 and 16.

12. The method according to claim 7, wherein n is an integer between 2 and 7.

13. The method according to claim 1, wherein said method comprises the treatment of wrinkles, scars or skin defects.

14. The method according to claim 13, wherein said hyaluronic acid compound functionalized with S-nitrosothiol groups is administered in the form of an injectable gel, a hydrogel, cream, dressing or film for topical application.

* * * * *

UNITED STATES PATENT AND TRADEMARK OFFICE
CERTIFICATE OF CORRECTION

PATENT NO. : 8,969,320 B2
APPLICATION NO. : 13/757720
DATED : March 3, 2015
INVENTOR(S) : Davide Renier et al.

Page 1 of 1

It is certified that error appears in the above-identified patent and that said Letters Patent is hereby corrected as shown below:

ON THE TITLE PAGE:

At item (62), Related U.S. Application Data, change

"Division of application No. 12/655,151, filed as application No. PCT/EP2008/005140 on Jun. 25, 2008, now abandoned."

to --Division of application No. 12/665,151, filed as application No. PCT/EP2008/005140 on Jun. 25, 2008, now abandoned.--

Signed and Sealed this
Fifteenth Day of September, 2015

Michelle K. Lee
*Director of the United States Patent and Trademark Office*